United States Patent [19]
Kroll et al.

[11] Patent Number: 5,913,877
[45] Date of Patent: Jun. 22, 1999

[54] IMPLANTABLE DEFIBRILLATOR SYSTEM FOR GENERATING A BIPHASIC WAVEFORM WITH ENHANCED PHASE TRANSITION

[76] Inventors: Mark W. Kroll, 13011 Brenwood Trail, Minnetonka, Minn. 55343; James E. Brewer, 2452 Southcrest Dr., Maplewood, Minn. 55119; Brad D. Pedersen, 4625 Washburn Ave. South, Minneapolis, Minn. 55410

[21] Appl. No.: 08/920,653

[22] Filed: Aug. 15, 1997

Related U.S. Application Data

[63] Continuation of application No. 08/613,854, Mar. 11, 1996, abandoned.

[51] Int. Cl.$^6$ .................................................. A61N 1/39
[52] U.S. Cl. ............................................... 607/5; 607/7
[58] Field of Search ...................................... 607/5, 7

[56] References Cited

U.S. PATENT DOCUMENTS

| | | |
|---|---|---|
| 4,637,397 | 1/1987 | Jones et al. . |
| 4,800,883 | 1/1989 | Winstrom . |
| 4,821,723 | 4/1989 | Baker, Jr. et al. ..................... 607/7 |
| 5,199,429 | 4/1993 | Kroll et al. . |
| 5,360,435 | 11/1994 | DeGroot ................................. 607/7 |
| 5,385,575 | 1/1995 | Adams ................................... 607/5 |
| 5,411,525 | 5/1995 | Swanson et al. ...................... 607/5 |
| 5,507,781 | 4/1996 | Kroll et al. . |
| 5,527,346 | 6/1996 | Kroll ..................................... 607/5 |
| 5,534,015 | 7/1996 | Kroll et al. . |
| 5,591,209 | 1/1997 | Kroll . |
| 5,601,608 | 2/1997 | Mouchawar . |
| 5,833,712 | 11/1998 | Kroll et al. . |
| 5,871,505 | 2/1999 | Adams et al. . |

OTHER PUBLICATIONS

*Improved defibrillation thresholds with large contoured epicardial electrodes and biphasic waveforms* Dixon EG, et al. Circulation 1987:76:1176–1184.

*Comparison of the internal defibrillation thresholds for monophasic and double and single capacitor biphasic waveforms* Kavanagh KM, et al. J Am Coll Cardiol 1989:14:1343–1349.

*Strength–duration and probability of success curves for defibrillation with biphasic waveforms.* Feeser SA, et al. Circulation 1990:82:2128–2141.

"Large Change in Voltage at Phase Reversal Improves Biphasic Defibrillation Thresholds Parallel–Series Mode Switching", Yamanouchi, Y et al, Circulation 1996:94:1768–1773, Oct. 1996.

(List continued on next page.)

*Primary Examiner*—William E. Kamm
*Assistant Examiner*—Carl H. Layno
*Attorney, Agent, or Firm*—Brad Pedersen

[57] ABSTRACT

A method and apparatus for generating biphasic waveforms uses an implantable cardioverter defibrillator (ICD) system having a phase transition enhancing capacitor system in addition to the capacitor system(s) which deliver the first and second phase of the biphasic countershock. Preferably, the ICD system has at least three capacitor systems and a capacitor switching network. The three capacitor systems include two primary capacitor systems and a third high voltage phase transition enhancing capacitor system having a time constant shorter than the time constant of the two primary capacitor systems. A first phase of the biphasic waveform preferably is produced by configuring the two primary capacitor systems to selectively discharge first in a parallel combination, and then in a series combination. The second phase of the biphasic waveform preferably is produced by reconfiguring the two primary capacitor systems to discharge in a parallel combination with reversed polarity. The phase transition enhancing capacitor system is selectively switched into the discharge of the biphasic waveform so as to effectively increase the voltage differential seen by the heart during the transition between the first and second phases of the biphasic waveform.

26 Claims, 5 Drawing Sheets

OTHER PUBLICATIONS

"Optimized First Phase Tilt in 'Parallel–Series' Biphasic Waveform", Yamanouchi, Y, Journal of Cardiovascular Electrophysiology 1997:8:649–657, Jun. 1997.

Comparison of Biphasic and Monophasic shocks for Defibrillation Using a non thoracotomy System, Wyse et al. *Americal Journal of Cardiology* 1993: 71: 197–202.

A prospective Randomized Evaluation of Biphasic versus Monophasic Waveform Pulses on Defibrillation, Bardy et al. *American College of Cardiology*, 1989:14:728–733.

Decline in Defibrillation Thresholds, Kroll et al, *PACE* 1993, 16:1:213–217.

Improved Defibrillation Thresholds with large Contoured Epicardial Electrodes and Biphasic Waveforms, Dixon et al, *Circulation* 1987, 76:1176–1184.

Comparison of the Internal Defibrillation Thresholds for Monophasic and Double and Single Capacitor Biphasic Waveforms, Kavanagh et al, *J Am College Cardiol* 1989, 14:1343–1349.

Strength–duration and Probability of Success Curves for Defibrillation with Biphasic Waveforms, Feeser et al, *Circulation* 1990, 82:2128–2141.

IMPLANTABLE DEFIBRILLATOR SYSTEM FOR GENERATING A BIPHASIC WAVEFORM WITH ENHANCED PHASE TRANSITION

RELATED APPLICATIONS

This application is a continuation of U.S. application Ser. No. 08/613,854 filed Mar. 11, 1996, now abandoned, and is related to three co-pending patent applications filed in the United States Patent and Trademark Office, the first of which is entitled "AN IMPLANTABLE DEFIBRILLATOR SYSTEM FOR GENERATING A BIPHASIC WAVEFORM", Ser. No. 08/426,023, filed Apr. 21, 1995, now U.S Pat. No. 5,833,712; the second of which is entitled "METHOD AND APPARATUS FOR GENERATING BIPHASIC WAVEFORMS IN AN IMPLANTABLE DEFIBRILLATOR", Ser. No. 08/457,307, filed Jun. 1, 1995, now U.S. Pat. No. 5,871,505, which is a continuation of Ser. No. 08/132,634, filed Oct. 6, 1993, now abandoned; the third of which is entitled "IMPLANTABLE DEFIBRILLATOR SYSTEM WITH CAPACITOR SWITCHING CIRCUITRY", Ser. No. 08/292,354, filed Aug. 18, 1994, now U.S. Pat. No. 5,507,781, which is a continuation of Ser. No. 07/999,393, filed Dec. 31, 1992, now abandoned, which is a continuation-in-part of an application entitled "IMPLANTABLE DEFIBRILLATOR SYSTEM EMPLOYING CAPACITOR SWITCHING NETWORKS", Ser. No. 07/704,619, filed May 23, 1991, and now issued as U.S. Pat. No. 5,199,429, all of which are assigned the same assignee as the present invention, and the disclosure of each of which is hereby incorporated by reference.

FIELD OF THE INVENTION

The present invention relates to the field of implantable cardioverter defibrillator (ICD) systems. More particularly, the present invention is an ICD that generates a biphasic countershock having an enhanced phase transition between the two phases of the biphasic countershock.

BACKGROUND OF THE INVENTION

Implantable cardioverter defibrillator (ICD) systems deliver a high voltage electrical countershock to the heart in an attempt to correct or convert a detected cardiac dysrhythmia or fibrillation. Due to the limitations on size and power imposed by the fact that these systems must be self-contained implantable devices, all existing ICD systems generate an electrical countershock by charging a capacitor system to a high voltage from a low voltage battery and oscillator circuit. The battery is then switched out of the circuit and the electrical charge stored in the capacitor system is delivered as a truncated capacitive discharge through two or more implanted electrodes.

To date, there have been two basic kinds of discharge waveforms which have been used with ICD systems: monophasic waveforms and biphasic waveforms; both of which are delivered as a truncated capacitive discharge. Monophasic waveforms are comprised of a single monotonically decaying electrical pulse that is typically truncated before the capacitor system is completely discharged. Biphasic waveforms, on the other hand, are comprised of a decaying electrical pulse that has a pair of decaying electrical phases that are of opposite polarity. To generate a biphasic pulse an H-bridge switch circuit connected to the electrodes is used to switch the polarity of the two phases. In generating the biphasic pulse, a first phase is discharged from the capacitor system, much in the same manner as a monophasic pulse. At the point in time that the first pulse is truncated, the H-bridge switch circuit immediately reverses the discharge polarity of the capacitor system as seen by the electrodes to produce the second phase of the biphasic waveform that is of the opposite polarity. A typical example of the use of an H-bridge circuit to generate a biphasic waveform in an implantable defibrillator system is shown in U.S. Pat. No. 4,998,531.

Over the last twenty five years, it has been demonstrated that appropriately truncated biphasic waveforms can achieve defibrillation with significantly lower currents, voltages and energies than monophasic waveforms of similar durations. Kroll, M W et al., "Decline in Defibrillation Thresholds", *PACE* 1993; 16#1:213–217; Bardy, G H et al., "A Prospective Randomized Evaluation of Biphasic vs. Monophasic Waveform Pulses on Defibrillation Efficiency in Humans", *J American College of Cardiology*, 1989; 14:728–733; and Wyse, D G et al., "Comparison of Biphasic and Monophasic Shocks for Defibrillation using a Non-Thoracotomy System", *American J Cardiology* 1993; 71:197–202. These findings are of particular importance for implantable devices because of the direct relationship between the amount of energy required for defibrillation and the overall size of the implantable device, i.e., the lower the energy required for defibrillation, the smaller the device.

Numerous theories have been advanced to explain the improved efficiency of the biphasic waveform over the more conventional monophasic waveform. Although some of these theories may partly explain, or may act cooperatively to explain, the effect a biphasic waveform has on the heart, there is currently no single accepted theory which fully explains the advantages of the biphasic waveform over the monophasic waveform. As a result, there is little or no agreement on what factors might further improve the efficiency and operation of the biphasic waveform.

In U.S. Pat. No. 5,199,429, a system for delivering a novel biphasic waveform is described in which two capacitor systems are used to store the electrical charge for the electrical countershock. To generate this biphasic waveform, the capacitor systems are configured in parallel for delivering a first phase of the biphasic waveform and in series for delivering a second phase of the biphasic waveform.

In U.S. Pat. No. 5,871,505, a new model is presented for understanding why the biphasic waveform is more effective than a monophasic waveform. Applying this new model, another system for delivering a novel biphasic waveform is described in which two capacitor systems are used to store the electrical charge for the electrical countershock. A first phase of the biphasic waveform for this system is delivered from a first electrical charge stored in a first capacitor system, and a second phase of the biphasic waveform is delivered from a second electrical charge stored in a second capacitor system. To maximize the effectiveness of the biphasic waveform according to the new model, this system teaches that the second electrical charge should be of less energy and should be stored separate and distinct from the first electrical charge.

In U.S. Pat. No. 5,833,712, a method and apparatus for generating biphasic waveforms uses an implantable cardioverter defibrillator having two capacitor systems and a switching network. A first phase of the biphasic waveform is produced by configuring the two capacitor systems to selectively discharge first in a parallel combination, and then in a series combination. The second phase of the biphasic waveform is produced by reconfiguring the two capacitor systems in a parallel combination. By reverting to a parallel configuration for the second phase of the biphasic waveform, the output characteristics of the second phase of a biphasic waveform more closely matched the model for understanding the effectiveness of the biphasic waveform.

Although these systems for generating biphasic waveforms have significantly improved the overall effectiveness of the biphasic countershock as delivered by an ICD, it would be desirable to further improve the effectiveness of such biphasic waveforms.

SUMMARY OF THE INVENTION

The present invention provides a method and apparatus for generating biphasic waveforms using an implantable cardioverter defibrillator (ICD) system having a phase transition enhancing capacitor system in addition to the capacitor system(s) which deliver the first and second phase of the biphasic countershock. Preferably, the ICD system has at least three capacitor systems and a capacitor switching network. The three capacitor systems include two primary capacitor systems and a third phase transition enhancing capacitor system having a time constant shorter than the time constant of the two primary capacitor systems. A first phase of the biphasic waveform preferably is produced by configuring the two primary capacitor systems to selectively discharge first in a parallel combination, and then in a series combination. The second phase of the biphasic waveform preferably is produced by reconfiguring the two primary capacitor systems to discharge in a parallel combination with reversed polarity. The phase transition enhancing capacitor system is selectively switched into the discharge of the biphasic waveform so as to effectively increase the voltage differential seen by the heart during the transition between the first and second phases of the biphasic waveform.

The present invention takes advantage of an additional factor discovered in the model for understanding the effectiveness of the biphasic waveform, namely the positive impact of increased voltage differential between the first and second phases of a biphasic waveform coupled with a short time constant associated with this increased voltage differential. Many theories have been offered for the improved efficacy of the biphasic defibrillation waveform. The present invention is derived from the use of a unique quantitative model based on the theory that the function of the first phase of the biphasic waveform is to initially synchronize and capture as many of the heart cells as possible in the same manner as a conventional monophasic wave, and the function of the second phase is to prevent unstable and delayed response of heart cells which could desynchronize the electrical activity of the heart. The present invention expands on previous models by theorizing that there are two mechanisms provided by the second phase of a biphasic waveform which can decrease unstable and delayed responses of heart cells. In the previous models, it was assumed that the primary purpose of the second phase was to remove any residual charge from the cell membranes that may have been deposited by the first phase of the countershock in order to prevent delayed and unstable activations. In the expanded model of the present invention, it is theorized that the second phase can serve two purposes, first to remove residual charge so as to prevent subsequent spontaneous activation (as in the previous model), or secondly to advance heart cells sharply into stimulation. In this model, the role of the second phase depends upon where a given heart cell is in the cyclical phase cycle when the first phase of the biphasic waveform is delivered.

At the time a defibrillation countershock is delivered, it has been recognized that heart cells in phase 0 and phase 1 are refractory and generally not susceptible to stimulation, either by the defibrillation waveform or by a fibrillation activation wavefront. Heart cells in phase 4 are activated and can be relatively easily stimulated by an electrical field on the order of 0.5 V/cm. It is heart cells which are in phases 2 and 3 that are the most difficult to stimulate and thereby capture as part of the countershock. Often, heart cells in phases 2 and 3 require electrical fields on the order of 5–10 V/cm or more to ensure effective stimulation that will capture substantially all of such cells. While it is possible to consistently create electrical fields of these magnitudes near the electrodes used to deliver the defibrillation countershock, differences in physical anatomy and electrode placement make it difficult to insure that the necessary electrical fields are consistently created at all locations in the heart remote from the defibrillation electrodes.

The present invention theorizes that the second phase of a biphasic waveform is most effective when it reduces the number of heart cells remaining in phases 2 and 3 to as few as possible after delivery of the second phase of the biphasic waveform. The reduction of heart cells remaining in phases 2 and 3 at the end of a defibrillation countershock is normally accomplished by providing an electrical field of greater than 10 V/cm so as to insure stimulation of the heart cells, even in phases 2 and 3. Because not all heart cells may be subjected to a field this large, and because the electrical energy required to produce such an electrical field is larger than might otherwise be required, the present invention utilizes two other mechanism as part of the second phase of a biphasic countershock to decrease the number of heart cells remaining in phases 2 and 3 at the end of the defibrillation countershock. First, as described in the related applications, the present invention preferably provides for a longer duration, lower voltage second phase that serves to remove residual charge from phase 2 and phase 3 cells which did not have sodium channel activated during delivery of the first phase, thereby burping these cells back to their status quo and minimize the risk of a delayed or unstable activation. Second, the present invention simultaneously provides for a short duration, high voltage transition to the second phase that serves to take advantage of heart cells in phases 2 and 3 which are believed to have had sodium channels activated during delivery of the first phase so as bump these cells forward into an activation phase that more closely resembles a phase 4 activation where the cells can be activated by smaller electrical fields.

The model used by the present invention assumes that the effective current requirement of the first phase is a linear function of the calculated residual (after the second phase) cell membrane voltage squared for heart cells which are not effectively stimulated by either the first or second phases under the previous (burping) mechanism. The present invention uses this model to optimize the generation of biphasic waveforms for an implantable defibrillator having a first stage capacitance discharge preferably by a combination of a parallel and series configuration of at least two primary capacitor systems to produce the first phase of the biphasic waveform. This combination provides for a good balance of energy transfer from the capacitor systems to the heart and desired waveshape of the first phase. The second stage capacitance discharge preferably is accomplished by reconfiguring the two primary capacitor systems in parallel and reversing polarity so as to provide a relatively long duration, low voltage second phase. In keeping with the new mechanism, the transition stage between the first and second stage capacitance discharge is selectively augmented by switching in the high voltage, short time constant transition enhancing capacitor system so as increase the voltage differential between the end of the first phase and the beginning of the second phase without supplying a large amount of residual energy that would otherwise then need to be removed by the remaining portion of the second phase.

In accordance with a first aspect of the present invention, an implantable cardioverter defibrillator apparatus discharges a biphasic electrical countershock to an ailing human heart through at least two implantable electrodes located proximate the heart. The apparatus comprises a detection system for detecting a cardiac dysrhythmia, an internal power source for providing electrical energy, and a capacitance system, electrically connected between the power source and the electrodes, for storing electrical energy to generate a first phase and a second phase of the biphasic countershock. The capacitance system includes at least two capacitor units each having separably switchable cathodes and anodes and one of the capacitor units having a smaller time constant than a time constant of the other of the capacitor units. A control system is operatively coupled to the detection system, the power source and the capacitance system for controlling delivery of the first phase and second phase of the biphasic countershock from the capacitance system to the electrodes in response to the cardiac dysrhythmia. The control system operates such that the first phase has a first polarity across the electrodes and the second phase has a second polarity across the electrodes and the one of the capacitor units having the smaller time constant is discharged during a transition between the first phase and the second phase to increase a voltage differential between an end of the first phase and a beginning of the second phase as compared to a voltage differential which otherwise would have been generated during the transition by the other of the capacitor units.

In accordance with a second aspect of the present invention, a method is described for operating an implantable cardioverter defibrillator device implanted within a human patient and electrically connected to at least two implantable electrodes located proximate a human heart to treat a cardiac arrhythmia by (a) sensing for a cardiac dysrhythmia in a human patient, and (b) in response to a sensing of a cardiac arrhythmia, delivering a biphasic countershock. Step (b) including the steps of: (b1) charging a capacitive charge storage system to a high voltage charge value using a low voltage power source, the capacitive charge storage system including at least two capacitor units each having separably switchable cathodes and anodes, one of the capacitor units having a smaller capacitance value than the other of the capacitor units; (b2) discharging at least a first portion of the charge value stored in the other of the capacitor units through the electrodes to produce the first phase of the biphasic countershock; (b3) discharging at least a second portion of the charge value stored in the other of the capacitor units through the electrodes to produce the second phase of the biphasic countershock having an opposite polarity from the first phase; and (b4) discharging at least a portion of the charge value stored in the one of the capacitor units having the smaller capacitance value through the electrodes during a transition between the first phase and the second phase of the biphasic countershock.

DETAILED DESCRIPTION OF THE INVENTION

Figure 1:
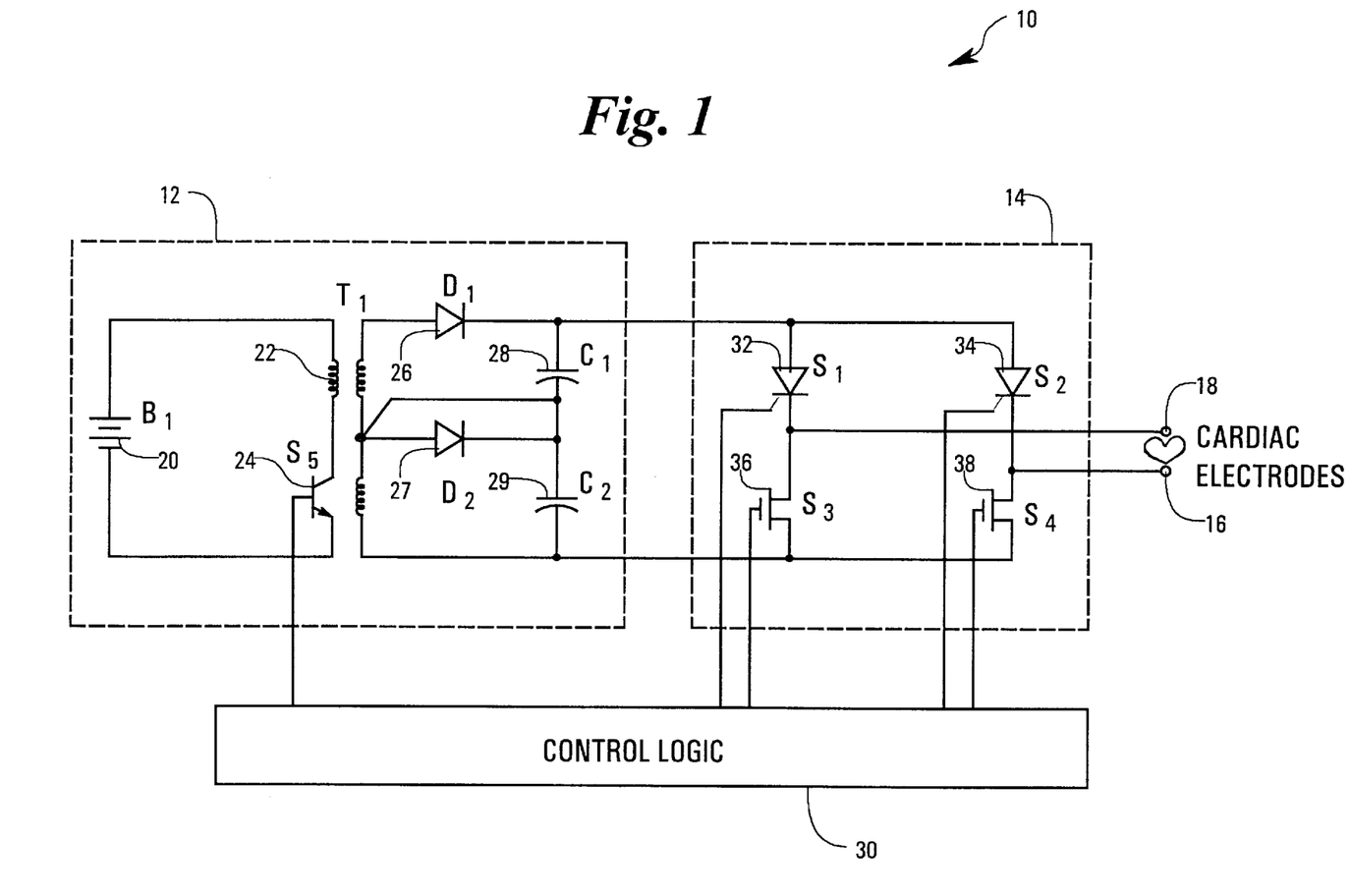
FIG. 1 is a schematic diagram of an ICD of the prior art.

In FIG. 1, a prior art example of an implantable cardioverter defibrillator (ICD) is depicted by circuitry 10 which includes a high output voltage circuit 12 selectively connected through an H-bridge switch 14 to cardiac electrodes 16, 18. High voltage circuit 12 is comprised of a battery power source 20, a secondary fly back transformer 22, transistor switch 24 and rectifying diodes 26, 27 that enable battery power source 20 to store a high voltage electrical charge in a high voltage storage capacitor system 28, 29 under control circuit logic 30. H-bridge 14 includes switch 32, switch 34, switch 36, and switch 38. The ICD monitors cardiac activity through sensing electrodes 42, 44 connected to a sensing/detection circuit 46 that is in turn connected to control logic 30.

Figure 2:
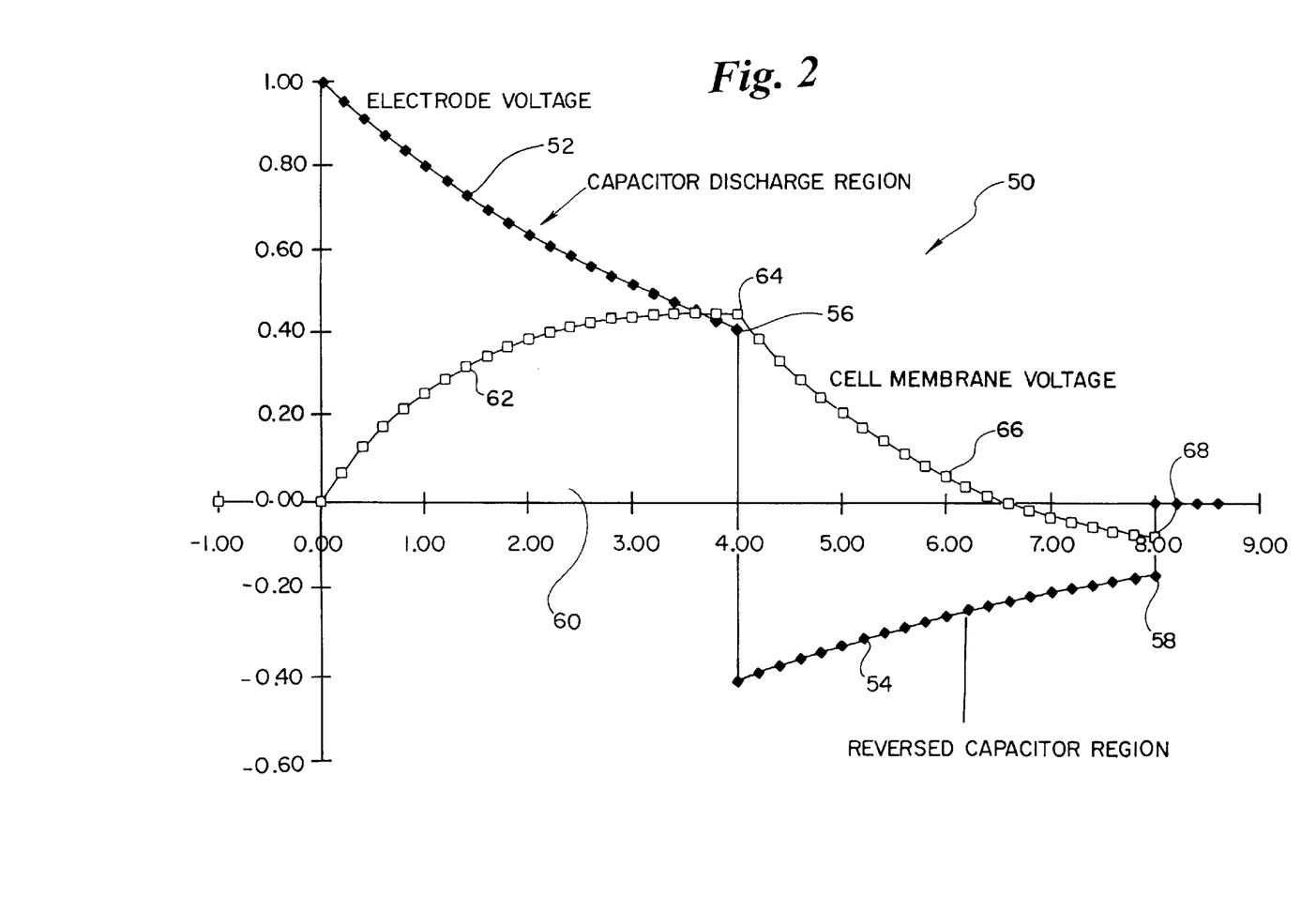
FIG. 2 depicts a representative voltage output for a biphasic waveform as generated by the ICD of FIG. 1.

A representative voltage output of the ICD circuit depicted in FIG. 1 is shown in FIG. 2. As shown in FIG. 2, output curve 50 has a upward first phase 52 and a downward second phase 54 with phase transition occurring at curve 56 and truncation of output at curve 58. A cell membrane voltage curve 60 is also shown in FIG. 2 depicting the cell membrane voltage response to the ICD output voltage shown in curve 50. A first phase curve 62 rises to transition 64 which corresponds to phase transition curve 56 at which time cell membrane voltage curve 60 enters a second phase 66 illustrating a decaying voltage to discharge truncation at 68.

It will be noted in FIG. 2 that output curve 50 decays from a normalized maximum voltage of 1.0 to about 0.42 of that voltage at about 4 ms at transition 56. The cell membrane voltage 60 is determined by theoretical calculations of the resulting cell membrane voltage in the heart cells when subjected to output curve 50. Cell membrane time constants for human heart cells are well documented in the medical research literature ranging from 1–6 ms, with 3 ms being the norm for most study results, so it is assumed for this calculation that the heart cells have an intrinsic time constant of about 3 ms. At transition 64, the cell membrane voltage has peaked at about 0.45 of its normalized maximum. During the second phase 54 of output curve 50, the second phase 66 of the cell membrane voltage discharges fairly rapidly and is restored to a zero voltage at about 6.5 ms.

For the reasons discussed in greater detail hereinafter, output curve 50 does not make optimal use of the electrical charge stored in capacitors 24, 26 for two reasons. First, the cell membrane is not fully charged until about 4 ms, as opposed to the theoretical optimal duration of the first phase which should be on the order of 2.4–3.0 ms, the "chronaxie" time for the human heart cell. Second, cell membrane voltage 60 is restored to zero volts by second phase 66, but is the "pulled through" zero volts such that the cell membrane is left with a negative voltage value at the truncation 58 of output curve 50.

The previous theoretical model suggested that the cell membrane voltage of any cells not stimulated by the countershock should be left at a voltage value very near zero at the end of a defibrillation countershock in order to prevent refibrillation. By doing so, it turns out that the amplitude requirements for the first phase of a biphasic countershock are effectively lowered. By not leaving the cell membrane voltage at a zero potential at the end of an electrical countershock, it is necessary that the electrical energy imparted to the heart cells by the first phase of the countershock must be greater so as to prevent any refilbrillation caused by the residual voltage on the cell membranes left at the end of the countershock.

Figure 3:
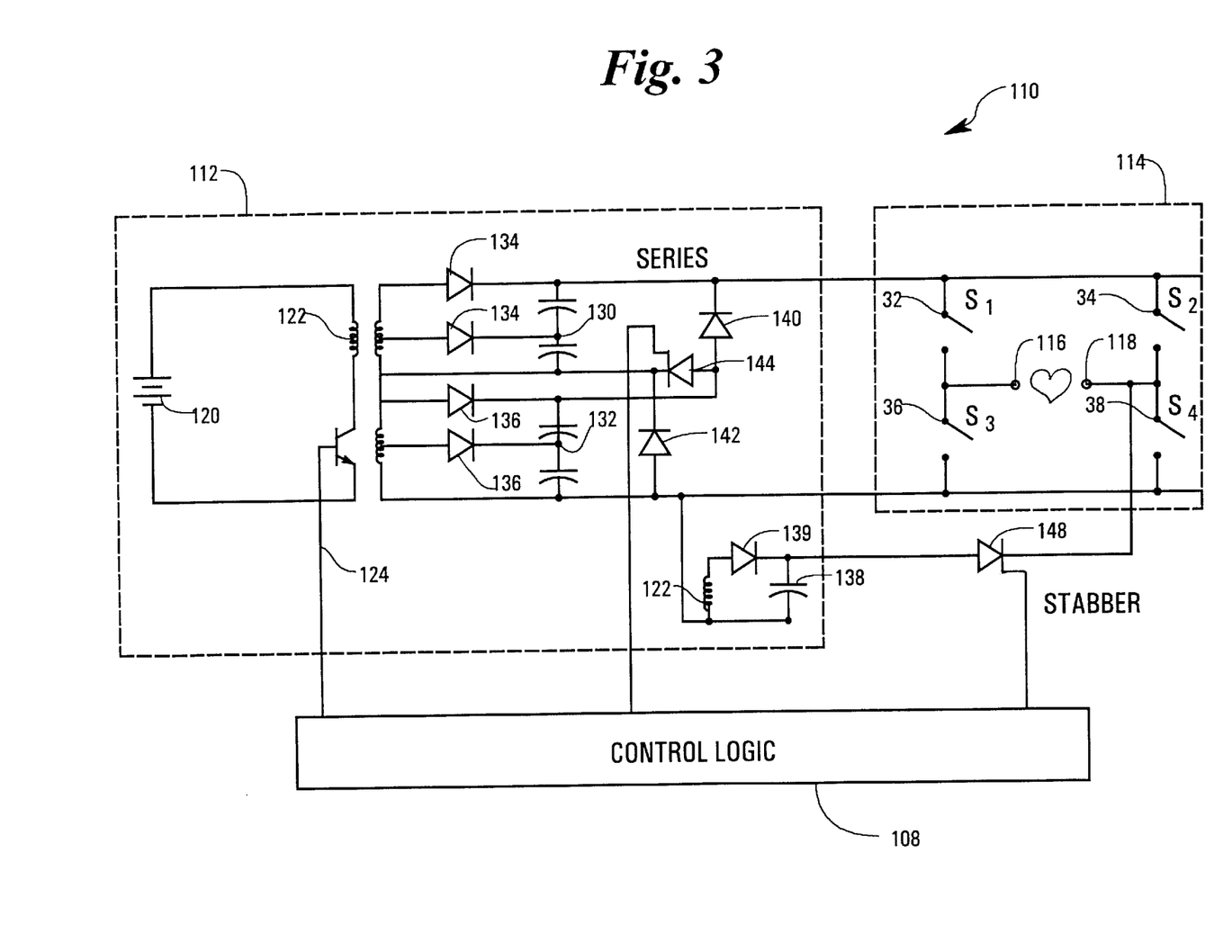
FIG. 3 is a schematic diagram of an ICD in accordance with the present invention.

Turning to FIG. 3 there is depicted an ICD 110 in accordance with a preferred embodiment of the present invention comprising a high voltage output circuit 112, H-bridge switch 114 and cardiac electrodes 116, 118. As with ICD 10 in the prior art, high output voltage circuit 112 includes a battery source 120, a secondary flyback transformer 122, and an oscillating transistor switch 124. Unlike ICD 10 in the prior art, ICD 110 includes at least two separate high voltage capacitor systems 130, 132 and a third transition enhancing capacitor system 138, all of which are coupled to transformer 122 by rectifying diodes 134, 136 and 139, respectively. Diodes 140 and 142 and SCR switch 144 provide a switching network under selective control of controller 108 that allows an output 150 across H-bridge switch 112 to be selectively configured as either a parallel or series combination of capacitor systems 130 and 132. Diode 134 and SCR switch 148 are also part of the switching network under selective control of controller 108 and provide the ability to selectively add the capacitive discharge of capacitor system 138 to output 150, either by itself or in addition to the outputs of capacitor systems 130 and 132. Controller 108 is preferably a microprocessor or microcontroller operating under software control, however, it will be recognized that controller 108 could also be implemented as discrete or integrated logic circuits. As with the prior art ICDs, the ICD of the present invention monitors cardiac activity through sensing electrodes 146, 147 connected to a sensing/detection circuit 148 that is in turn connected to controller 108. It will be apparent that any number of know sensing and detection circuits and techniques can be used with the present invention.

It should be noted that, in the preferred embodiment, capacitor systems 130 and 132 are preferably not merely a single capacitor system, but are each preferably implemented using, for example, two photoflash capacitors configured in series, each capable of storing up to a 375 V charge with a midpoint tap in transformer 122 and two rectifying diodes 134, 134', 136 and 136' each used to charge one of the two photoflash capacitors, respectively, that together comprise capacitor system 130 and 132. Each capacitor system 130, 132 and 138 is a capacitor arrangement that has separate accessible cathode and anode outputs that are independently switchable under control of controller 108. For example, each of capacitor systems 130 and 132 could be implemented as a pair of 60 μF photoflash capacitors in series, for a total of four photoflash capacitors used in high voltage circuit 112. Alternatively, capacitor systems 130 or 132 could be implemented as a single high voltage film capacitor or even as a combination of double layer capacitors. The time constant of capacitor systems 130 and 132 is preferably selected to be at least as great as the natural chronaxie of the human heart (2–4 ms). As such, capacitor systems 130 and 132 preferably have an effective capacitance value of at least 45 μF and preferably greater than 60 μF. Alternatively, capacitors with a lower effective capacitance and time constant could be used for capacitor systems 130 and 132 if a duration lengthening technique, such as taught in U.S. Pat. No. 5,391,186, is utilized.

Capacitor system 138 is preferably a single high voltage film capacitor having a smaller capacitance value, on the order of 45 μF or less, and preferably less than 30 μF. Alternatively, capacitor system 138 may be comprised of a single electrolytic cell, or two or more electrolytic cells electrically connected in series. Preferably, capacitor system 138 has a time constant that is less than 2 ms, and optimally less than 1 ms, so that the large voltage differential produced during the transition between the first and second phase of the biphasic countershock is not capacitively coupled by the inherent capacitance of the cell membrane.

Figure 4:
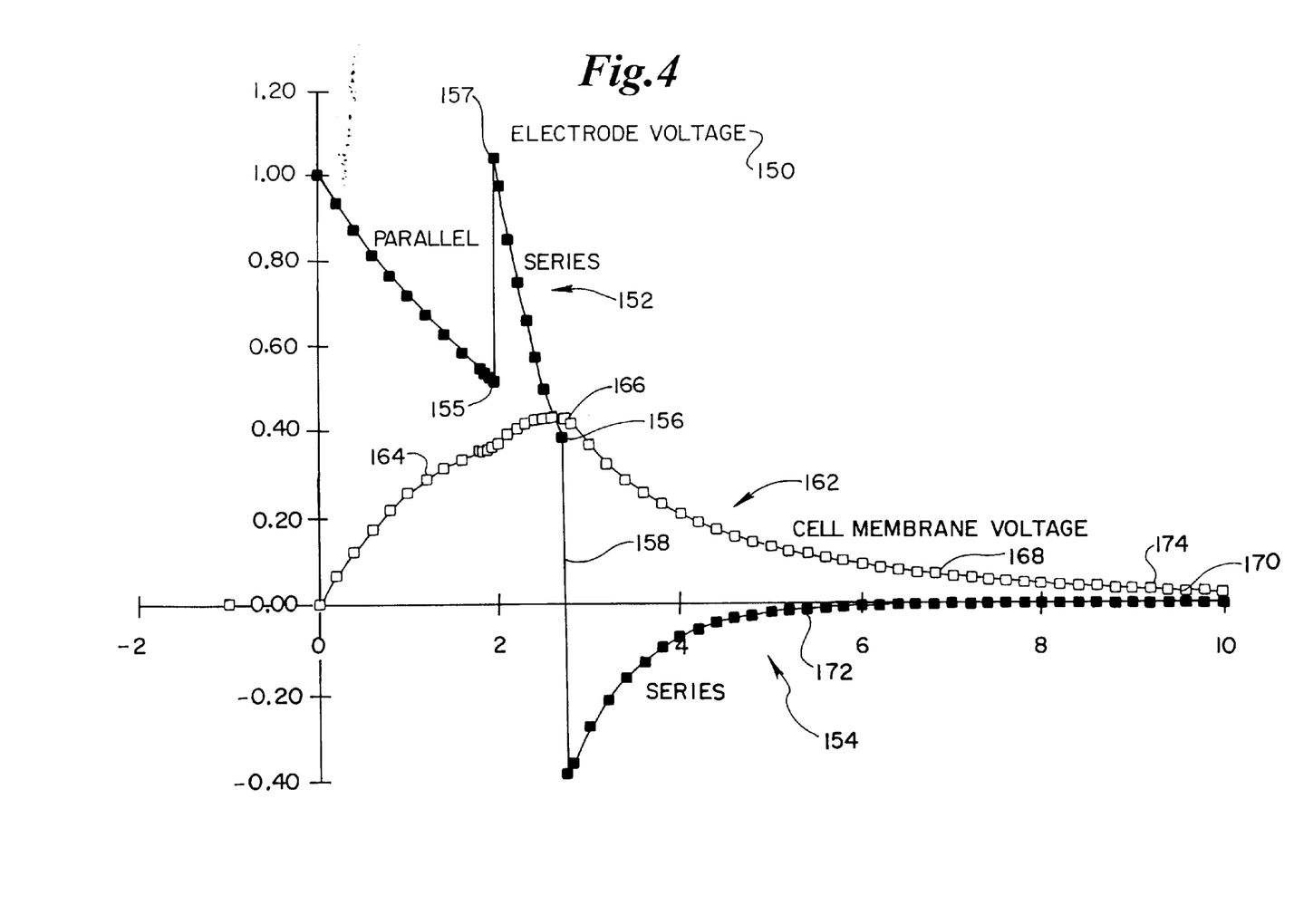
FIG. 4 depicts a representative voltage output for a biphasic waveform as generated in accordance with the previous theory for the biphasic model.

FIG. 4 discloses a representative output for a prior art ICD. As shown in FIG. 4, voltage output is characterized by curve 150 which includes a forward first phase 152 and an opposite second phase 154 separated by a transition period 158 with the entire biphasic waveform output ending at truncation 160. At the start of first phase 152, switch 144 (as shown in FIG. 3) is not enabled and capacitor systems 130 and 132 are configured in parallel so as to provide a normalized output voltage of 1.0 that decays to about 0.5 at about 2 ms. At point 155, capacitors 130, 132, are switched into a series configuration by enabling switch 144 so as to effectively double the voltage output at point 157 to slightly over 1.0 of the normalized maximum voltage. The series configuration is maintained for approximately 0.8 ms, at which point first phase 152 is truncated at point 156.

The preferred durations of the parallel and series portions of first phase 152 are determined based on an optimization analysis, however, it will be recognized that different durations of each portion may be used. Alternatively, more than two capacitor units 130, 132 may be used, in which case multiple combinations of parallel and series topology for the three or more capacitor units would be possible. It will also be appreciated that in this type of an output, transition 158 may be either an extremely short transition (e.g., less than 100 μs) in which point 156 is actively driven to a negative potential, or transition 158 may be a somewhat longer transition during which time point 156 is allowed to float relative to the ground or capacitor potential. During second phase 154, capacitors 130, 132 remain in a series configuration in this type of an output until truncation point 160.

Also depicted in FIG. 4 is cell membrane voltage curve 162 illustrating the cell membrane voltage response to the output of an ICD of the co-pending application. Cell membrane curve 162 includes a forward phase rising voltage curve 164 that reverses its rise at 166 which corresponds to high voltage truncation 156 on curve 150. During the reverse phase 154 cell membrane curve 168 decreases to 170 which corresponds to truncation 160 when the discharge of the second phase is completed.

Figure 5:
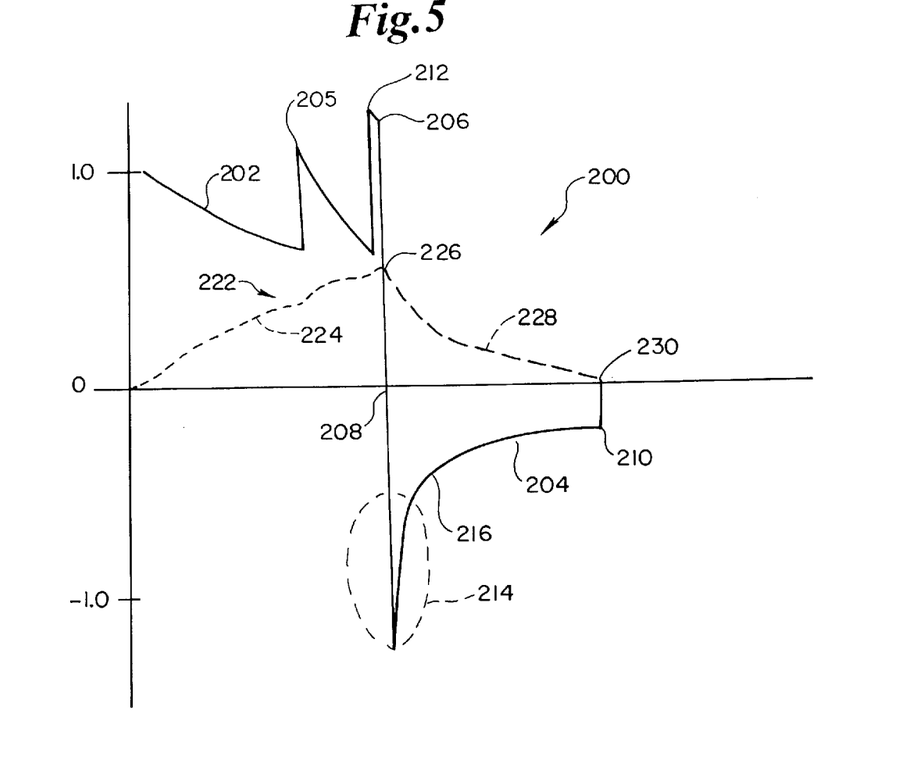
FIG. 5 depicts a representative voltage output for a first embodiment of a transition enhanced biphasic waveform as generated in accordance with the present invention.
Figure 6:
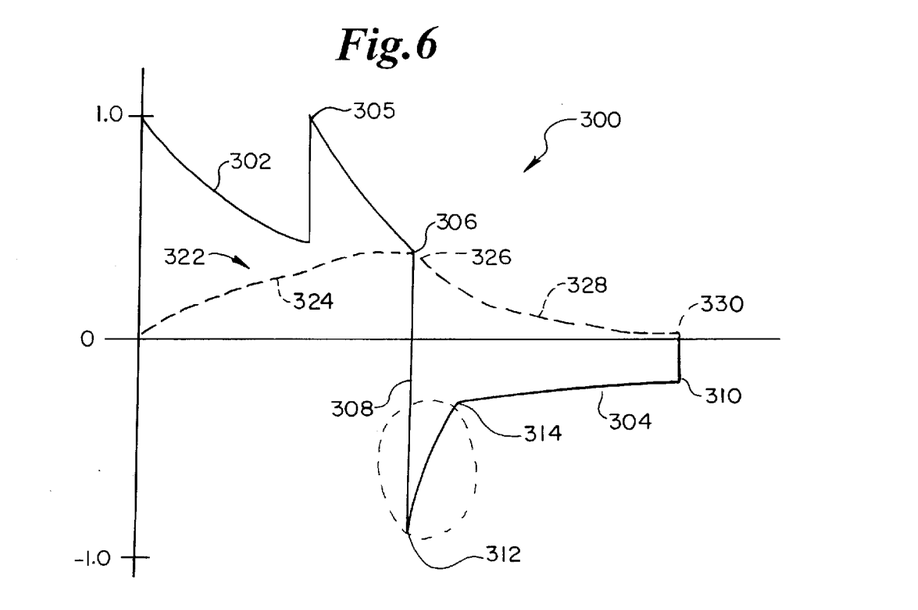
FIG. 6 depicts a representative voltage output for a second embodiment of a transition enhanced biphasic waveform as generated in accordance with the present invention.

FIGS. 5 and 6 disclose two representative outputs for an ICD in accordance with different preferred embodiments of the present invention. In general, each of these outputs is similar to the output as shown in FIG. 4, with the selective addition of the voltage output of capacitor system 138 under the programmable control of controller 108.

In a first embodiment shown in FIG. 5, the output of capacitor system 138 is selectively added to curve 200 just prior to an end 206 of a forward first phase 202 and before an opposite second phase 204 separated by a transition period 208. As with FIG. 4, the entire biphasic waveform output ends at truncation 210. At the start of first phase 202, switch 144 (as shown in FIG. 3) is not enabled and capacitor systems 130 and 132 are configured in parallel so as to provide a normalized output voltage of 1.0 that decays to just over 0.5 at about 2 ms. At point 205, capacitors 130, 132, are switched into a series configuration by enabling switch 144 so as to effectively double the voltage output at point 205 to slightly over 1.0 of the normalized maximum voltage. The series configuration is maintained for approximately 0.8 ms, at which point enabling switch 148 is switched into the output to add the output of capacitor system 138 to curve 200 at a point 212 just prior to where first phase 202 is truncated at point 206. In this embodiment, the operation of H-bridge switch would need to be reversed from normal operation, or alternatively, switch 148 should be connected to node 116, rather than node 118.

In this embodiment, the voltage output at point 212 again rises to a voltage equal to 1.0 of the normalized maximum voltage, due to the fact that enabling switch 144 is turned off, such that point 212 is solely generated by the voltage output of capacitor system 138. Alternatively, enabling switch 144 may be left on, such that point 212 is generated by the series combination of capacitor system 130, 132 in parallel with capacitor system 138. It will be apparent that, depending upon the charging voltage values of capacitor system 138 and depending upon whether enabling switch 144 is turned off or left on, or whether additional switches are added to alter the topology of capacitor systems 130, 132, and 138, the voltage values and discharge time constants for the transition enhancing portion 214 of curve 200 can be manipulated to various combinations.

In this embodiment, capacitor system 138 is preferably comprised of a pair of high voltage, 2.5 $\mu$F thin film capacitors which are first arranged in series and charged to an effective charging voltage of 1500 V and a total charging energy of 1.4 J, and are then arranged in parallel to be discharged at an effective discharge voltage of 750 V with an effective discharge capacitance of 5 $\mu$F. (circuitry not shown). Thus, for a 50 $\Omega$ assumed myocardial resistance, the discharge time constant (tau) of capacitor system 138 is 0.25 ms. In this embodiment, controller 108 turns off switch 144 and turns on switch 148 for a period of 50 $\mu$s, for example, at the end of first phase 202, and, after the transition period 208, discharges the remaining 200 $\mu$S of the transition enhancing period 214 at the start of second phase 204. At the end 216 of the transition enhancing period 214, enabling switch 144 is again turned on and the series combination of capacitor systems 130, 132 and 138 are discharged until truncation at point 206. At point 216, the voltage value on all three capacitor systems is approximately equal to 250 V and the effective capacitance of the combination of the three capacitor systems 130, 132 and 138 will be 65 $\mu$F.

Cell membrane curve 222 includes a forward phase rising voltage curve 224 that reverses its rise at 226 which corresponds to transition period 208 on curve 200. During the reverse phase 204 cell membrane curve 228 decreases to 230 which corresponds to truncation 210 when the discharge of the second phase is completed. The duration from point 216 to truncation 206 is preferably optimized such that a residual membrane potential at the end of the reverse phase as shown at 230 is equal to zero. In this embodiment, the optimum duration is estimated to be equal to the time constant remaining at point 216, such that the total duration of the second phase 204 is equal to 3.45 ms and the final voltage at truncation 206 is equal to 82.5 V. In this embodiment, the total energy delivered by the second phase is estimated to be 1.125 J.

It can be seen in this embodiment that the voltage differential generated during the transition phase 208 is approximately 1500 V (+750 V to –750 V). This voltage differential is contrasted to the voltage differential shown in FIG. 4 of only 560 V (+255 V to –255 V) or 545 V in a classic biphasic model with a first phase truncated at 66% tilt (+247 V to –247 V). It is theorized that for the present invention to be significant in reducing the amount of energy needed for consistently successful defibrillation, the voltage differential generated during transition phase 208 preferably should be equal to or greater than the normalized voltage (e.g., 750 V) such that the cell membrane voltage effectively see a complete voltage reversal between the first phase 202 and second phase 204.

In a second embodiment shown in FIG. 6, the output of capacitor system 138 is selectively added to curve 300 just after an end 306 of a forward first phase 302 and at the start of an opposite second phase 304 separated by a transition period 308. As with FIG. 4, the entire biphasic waveform output ends at truncation 310. At the start of first phase 302, switch 144 (as shown in FIG. 3) is not enabled and capacitor systems 130 and 132 are configured in parallel so as to provide a normalized output voltage of 1.0 that decays to about 0.5 at about 2 ms. At point 305, capacitors 130, 132, are switched into a series configuration by enabling switch 144 so as to effectively double the voltage output at point 307 to slightly over 1.0 of the normalized maximum voltage. The series configuration is maintained for approximately 0.8 ms, at which point first phase 302 is truncated at point 306. After the polarity of the countershock has been reversed during transition 208, enabling switch 148 is turned on such that the output voltage of capacitor system 138 is added to the output voltages of capacitor systems 130 and 132.

In this embodiment, the voltage output at point 312 at the start of second phase 304 will be a voltage equal to 0.83 of the normalized maximum voltage, due to the fact that enabling switch 144 may be left on, such that point 212 is generated by the series combination of capacitor systems 130, 132 in parallel with capacitor system 138. Alternatively, enabling switch 144 may be turned off, such that point 312 is solely generated by the voltage output of capacitor system 138. In still another embodiment, capacitor systems 130, 132 and 138 could be reconfigured into a fully parallel topology to increase the duration of second phase 304. Again, it will be apparent that, depending upon the charging voltage values of capacitor system 138 and depending upon whether enabling switch 144 is turned off or left on, or whether additional switches are added to alter the topology of capacitor systems 130, 132, and 138, the voltage values and discharge time constants for the transition enhancing portion 314 of curve 300 can be manipulated to various combinations.

In this embodiment, capacitor system 138 is preferably comprised of a pair of 20 $\mu$F electrolytic capacitor charged to an effective charging voltage for each of 375 V and a total charging energy of 1.4 J. The total available energy for the combination of capacitor systems 130, 132, and 138 is about 1.88 J with an effective capacitance of 35 $\mu$F. Thus, for a 50 $\Omega$ assumed myocardial resistance, the discharge time constant (tau) of capacitor systems 130, 132, and 138 is 1.75 ms. In this embodiment, controller 108 turns off switches 144 and 148 at the truncation of curve 300 at point 306

Cell membrane curve 322 includes a forward phase rising voltage curve 324 that reverses its rise at 326 which corresponds to transition period 308 on curve 300. During the reverse phase 304 cell membrane curve 328 decreases to 330 which corresponds to truncation 310 when the discharge of the second phase is completed. The duration of second phase 304 until truncation 310 is preferably optimized such that a residual membrane potential at the end of the reverse phase as shown at 330 is equal to zero. In this embodiment, the optimum duration is estimated to be 4 ms and the final voltage at truncation 310 is equal to −30 V.

It can be seen in this embodiment that the voltage differential generated during the transition phase 208 is approximately 855 V (+255 V to −630 V). Again, this voltage differential is contrasted to the voltage differential shown in FIG. 4 of only 560 V (+255 V to −255 V) or 545 V in a classic biphasic model with a first phase truncated at 66% tilt (+247 V to −247 V) and is equal to or greater than the normalized voltage (e.g., 750 V) for the ICD system.

It should be noted that due to this increased voltage differential, capacitive coupling problems can be induced within the circuitry internal to the ICD system if the housing of the ICD system is utilized as one of the electrodes. Accordingly, the present invention contemplates the use of an internal ICD shield, or the use of a slew-rate limiting circuit.

It should also be noted that controller 108 can be configured to control the discharge of first phase 152 in response to a variety of preprogrammed criteria maintained by controller 108, including changing topology as a function of a fixed duration, a fixed tilt, minimum duration, minimum tilt, or any combination thereof, including a minimum of either a fixed duration or a fixed tilt. Similarly, controller 108 can also control second phase 154 so as to truncate this phase if necessary in the event that cell membrane voltage 180 returns to a zero residual voltage prior to the complete discharge of capacitors 130, 132 in the series topology configuration.

We claim:

1. An implantable cardioverter defibrillator apparatus for discharging a biphasic electrical countershock to an ailing human heart through at least two implantable electrodes located proximate the heart, the apparatus comprising:

a detection system for detecting a cardiac dysrhythmia;

an internal power source for providing electrical energy;

a capacitance system, electrically connected between the power source and the electrodes, for storing electrical energy to generate a first phase and a second phase of the biphasic countershock, the capacitance system including at least two capacitor units each having separably switchable cathodes and anodes and one of the capacitor units having a smaller time constant than a time constant of the other of the capacitor units; and a control system, operatively coupled to the detection system, the power source and the capacitance system, for controlling delivery of the first phase and second phase of the biphasic countershock from the capacitance system to the electrodes in response to the cardiac dysrhythmia such that the first phase has a first polarity across the electrodes and the second phase has a second polarity across the electrodes and the one of the capacitor units having the smaller time constant is discharged during a transition between the first phase and the second phase to increase a voltage differential between an end of the first phase and a beginning of the second phase.

2. The apparatus of claim 1 wherein the capacitor system includes at least three capacitor units, at least two of the capacitor units being primary capacitor units and a third capacitor unit being a transition enhancing capacitor unit having the smaller time constant, and wherein the primary capacitor units are discharged being configured first in a parallel configuration and then in a series configuration during the first phase and are discharged being configured in a parallel configuration during the second phase.

3. The apparatus of claim 2 wherein the primary capacitor units are each of which is comprised of a pair of electrolytic capacitors electrically connected in series.

4. The apparatus of claim 2 wherein the control system controls delivery of the second phase such that a first portion of the second phase is delivered only from the transition enhancing capacitor and a remaining portion of the second phase is delivered from the primary capacitor units.

5. The apparatus of claim 2 wherein the control system controls delivery of the biphasic countershock such that an output of the transition enhancing capacitor is selectively added to an output delivered from the primary capacitor units.

6. The apparatus of claim 1 wherein the capacitor unit having the smaller time constant is selected from the set consisting of: an electrolytic capacitor, a pair of electrolytic capacitors electrically connected in series, and a film capacitor.

7. The apparatus of claim 1 wherein the control system selectively discharges the capacitor unit having the smaller time constant at a time selected from the set consisting of: just prior to the transition, at the transition and just after the transition.

8. The apparatus of claim 1 wherein the control system controls a duration and a topology for the first phase and the second phase in response to a preprogrammed criteria selected from the set consisting of: a fixed duration, a fixed tilt, a minimum duration, a minimum tilt, and any combination thereof.

9. The apparatus of claim 1 wherein a voltage differential between the first phase and the second phase is equal to or greater than an initial voltage of the first phase.

10. An implantable cardioverter defibrillator apparatus for discharging a biphasic electrical countershock to an ailing human heart through at least two implantable electrodes located proximate the heart, the apparatus comprising:

a detection system for detecting a cardiac dysrhythmia;

an internal power source for providing electrical energy;

a capacitance system, electrically connected between the power source and the electrodes, for storing electrical energy to generate a first phase and a second phase of the biphasic countershock, the capacitance system including at least two capacitor units each having separably switchable cathodes and anodes, one of the capacitor units having a smaller time constant than a time constant of the other of the capacitor units; and a control system, operatively coupled to the detection system, the power source and the capacitance system, for controlling delivery of the first phase and second phase of the biphasic countershock from the capacitance system to the electrodes in response to the cardiac dysrhythmia such that the other of the capacitor units are discharged in opposite polarities across the electrodes during the first phase and the second phase and that the one of the capacitor units having the smaller time constant is discharged for only a first portion of the second phase.

11. The apparatus of claim 10 wherein the capacitance system includes at least three capacitor units, at least two of the capacitor units being primary capacitor units and a third capacitor unit being a transition enhancing capacitor unit having the smaller time constant, and wherein the primary capacitor units are discharged being configured first in a parallel configuration and then in a series configuration during the first phase and are discharged being configured in a parallel configuration during the second phase.

12. The apparatus of claim 11 wherein the primary capacitor units are each of which is comprised of a pair of electrolytic capacitors electrically connected in series.

13. The apparatus of claim 11 wherein the control system controls delivery of the second phase such that a first portion of the second phase is delivered only from the transition enhancing capacitor and a remaining portion of the second phase is delivered from the primary capacitor units.

14. The apparatus of claim 11 wherein the control system controls delivery of the biphasic countershock such that an output of the transition enhancing capacitor is selectively added to an output delivered from the primary capacitor units.

15. The apparatus of claim 10 wherein the capacitor unit having the smaller time constant is selected from the set consisting of: an electrolytic capacitor, a pair of electrolytic capacitors electrically connected in series, and a film capacitor.

16. The apparatus of claim 10 wherein the control system selectively discharges the capacitor unit having the smaller time constant at a time beginning from a time selected from the set comprising: just prior to the transition, at the transition and just after the transition.

17. The apparatus of claim 10 wherein the control system controls a duration and a topology for the first phase and the second phase in response to a preprogrammed criteria selected from the set consisting of: a fixed duration, a fixed tilt, a minimum duration, a minimum tilt, and any combination thereof.

18. The apparatus of claim 10 wherein a voltage differential between the first phase and the second phase is equal to or greater than an initial voltage of the first phase.

19. A method for operating an implantable cardioverter defibrillator device implanted within a human patient and electrically connected to at least two implantable electrodes located proximate a human heart to treat a cardiac arrhythmia by delivering an electrical countershock, the method comprising the device-implemented steps of:

(a) sensing for a cardiac dysrhythmia in a human patient;

(b) in response to a sensing of a cardiac arrhythmia, performing the steps of:

(b1) charging a capacitive charge storage system to a high voltage charge value using a low voltage power source, the capacitive charge storage system including at least two capacitor units each having separably switchable cathodes and anodes, one of the capacitor units having a smaller capacitance value than the other of the capacitor units;

(b2) discharging at least a first portion of the charge value stored in the other of the capacitor units through the electrodes to produce the first phase of the biphasic countershock;

(b3) discharging at least a second portion of the charge value stored in the other of the capacitor units through the electrodes to produce the second phase of the biphasic countershock having an opposite polarity from the first phase; and (b4) discharging at least a portion of the charge value stored in the one of the capacitor units having the smaller capacitance value through the electrodes during a transition between the first phase and the second phase of the biphasic countershock.

20. The method of claim 19 wherein the other of the capacitor units include at least two capacitor units with separably switchable cathodes and anodes and wherein step (b2) is performed with the at least two capacitor units configured first in parallel and then in series and step (b3) is performed with the at least two capacitor units configured in parallel.

21. The method of claim 19 further comprising a step of preprogramming selected criteria to establish a duration for the first phase selected from the set consisting of: a fixed duration, a fixed tilt, a minimum duration, a minimum tilt, or any combination thereof.

22. The method of claim 19, further comprising a step of preprogramming selected criteria to establish a duration for the second phase selected from the set consisting of: a fixed duration, a fixed tilt, a minimum duration, a minimum tilt, or any combination thereof.

23. The method of claim 19 wherein step (b4) is performed at a starting time selected from the set consisting of: an end of the first phase, the transition between the first phase and the second phase, and a start of the second phase.

24. The method of claim 19 wherein steps (b3) and (b4) are performed such that a first portion of the second phase is delivered only from the capacitor having the smaller capacitance value and a remaining portion of the second phase is delivered from the other of the capacitor units.

25. The method of claim 19 wherein steps (b2), (b3) and (b4) are performed such that an output of the capacitor having the smaller capacitance value is selectively added to an output delivered from the other of the capacitor units.

26. The method of claim 19 wherein steps (b2), (b3) and (b4) are performed such that a voltage differential between the first phase and the second phase is equal to or greater than an initial voltage of the first phase.

* * * * *